United States Patent [19]

Takagi

[11] Patent Number: 5,235,627
[45] Date of Patent: Aug. 10, 1993

[54] X-RAY DIAGNOSTIC SYSTEM

[75] Inventor: Michio Takagi, Tokyo, Japan

[73] Assignee: Kabushiki Kaisha Toshiba, Tokyo, Japan

[21] Appl. No.: 832,726

[22] Filed: Feb. 7, 1992

[30] Foreign Application Priority Data

Feb. 7, 1991 [JP] Japan .................................. 3-15617

[51] Int. Cl.$^5$ .............................................. G21K 1/04
[52] U.S. Cl. ................................... 378/151; 378/195; 378/94; 378/145
[58] Field of Search ................. 378/151, 94, 159, 150, 378/193, 145, 195, 197, 19, 58, 95

[56] References Cited

U.S. PATENT DOCUMENTS 3,947,689 3/1976 Wagner .
4,935,946 6/1990 Hefter et al. ........................ 378/151
4,991,189 2/1991 Boomgaarden et al. .

FOREIGN PATENT DOCUMENTS 0083756 7/1983 European Pat. Off. .
0284733 10/1988 European Pat. Off. .
0333256 9/1989 European Pat. Off. .

*Primary Examiner*—David P. Porta
*Assistant Examiner*—Don Wong
*Attorney, Agent, or Firm*—Oblon, Spivak, McClelland, Maier & Neustadt

[57] ABSTRACT

In order to compensate offsets in an X-ray irradiated field, an X-ray diagnostic system comprises: an X-ray source including a movable X-ray diaphram unit; an X-ray camera unit for radiographing a patient as an object; a holding means for holding the X-ray tube and the X-ray camera unit in opposition and maintaining sufficient operating space between them; a seeking means for seeking a offset in an X-ray irradiated field; a controlling means for controlling the X-ray diaphragm unit according to an output of the seeking means.

7 Claims, 6 Drawing Sheets

X-RAY DIAGNOSTIC SYSTEM

BACKGROUND OF THE INVENTION

1. Field of the Invention

This invention relates generally to an X-ray diagnostic system, and is concerned in particular with a diagnostic system with an X-ray camera supported by an arm, which is provided with a system for compensating offsets in an X-ray irradiated field.

2. Description of the Prior Art

A conventional X-ray diagnostic system, such as a system for diagnosing circulatory organs includes an arm which supports an X-ray source such as an X-ray tube at one end and an X-ray camera opposing the X-ray tube at the other end. The arm is usually formed in a C-shape or an Ω-shape in order to maintain sufficient inner space to permit the X-ray tube and X-ray camera to be set at various positions around the patient.

However, a large arm bends from the weight of an X-ray tube and its accessories, and causes offsets in the X-ray irradiated field.

As a result of the offsets, not only the required part radiographed is, but also parts of the patient are irradiated inadvertently when an autocollimator is used. This problem become more serious when larger the X-ray diagnostic systems are used.

Conventional systems solve the above-mentioned problems in the following manner;

(i) Utilization of an arm with more rigid members to reduce the amount of bending.

(ii) Changing the location and angle at which heavy devices such as an X-ray tube, an X-ray diaphragm device or an image intensifier are attached so that the amount of bending is decreased.

However, it is not always possible to utilize large and rigid arms, because these require a lot of space and as a result insufficient space is provided for operating the devices. In the future, X-ray diaphragm devices and image intensifiers are expected to become larger and heavier, thus exacerbating the problem will be more serious. It is very difficult to eliminate the offsets of the X-ray irradiated field for every position and angle of the arm simply by changing the locations and angles at which the image intensifier or the X-ray tube are attached.

Therefore, the use of a conventional X-ray diagnostic system with a large arm leads to substantial offsets in the irradiated field. This makes it difficult to irradiate at an exact location and to prevent unwanted irradiation of the patient.

SUMMARY OF THE INVENTION

The present invention has been made in an attempt to solve the above-described drawbacks, and therefore has an object of providing an X-ray diagnostic system that makes it possible to eliminate offsets in X-ray irradiated fields when a holding arm is used for a large X-ray diagnostic system.

An X-ray diagnostic system of the invention comprises an X-ray camera unit for radiographing a patient as an object; a holding means for holding the X-ray tube and the X-ray camera unit in opposition and maintaining sufficient operating space between them; a seeking means for seeking a offset in an X-ray irradiated field; a controlling means for controlling the X-ray diaphragm unit according to an output of the seeking means.

Preferably, the seeking means comprises a first measuring device for measuring an angle of rotation of the arm around an axis of the patient, a second measuring device for measuring an angle of rotation of the arm in a plane including the axis, and a third measuring device for measuring a distance SID.

Preferably, the movable X-ray diaphragm unit includes a plurality of movable wings for limiting an X-ray irradiated field.

Preferably, the controlling means is provided with a compensating table for calculating compensating amounts according to data from the seeking means, and further provided with a seeking means for seeking compensating amounts experimentally according to data from the seeking means and the offsets of the X-ray irradiated field.

These and other objects, features and advantages of the present invention will be more apparent from the following description of a preferred embodiment, taken in conjunction with the accompanying drawings.

DETAILED DESCRIPTION OF THE EMBODIMENT

Figure 1:
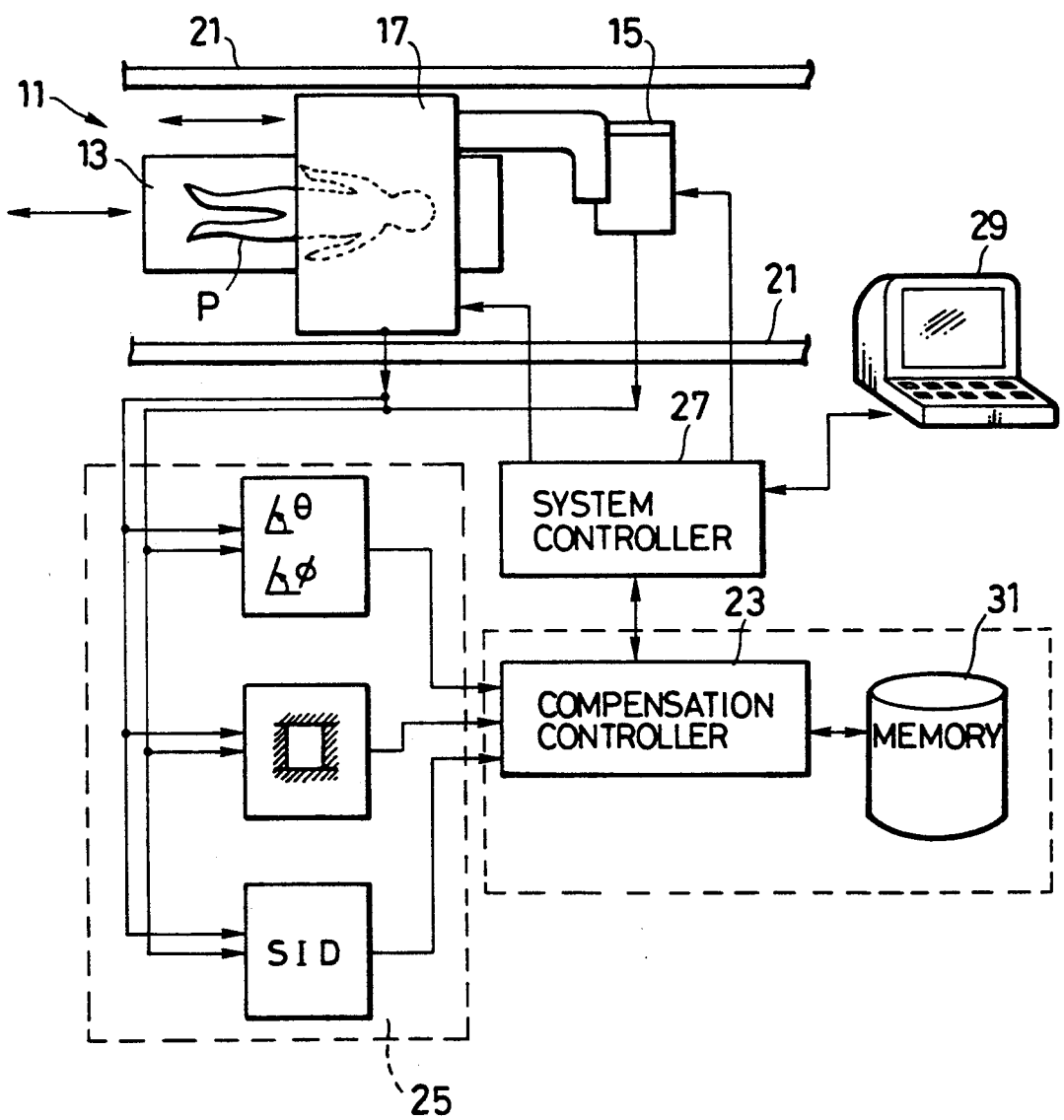
FIG. 1 is a schematic block diagram of the first embodiment of the present invention.

FIG. 1 is a schematic block diagram of the first embodiment of the present invention. In the figure, an X-ray diagnostic system of the present invention comprises a catheter table 13 on which a patient P is laid, a first supporting system 15 installed on the floor closed to the top end of the catheter table 13, a second supporting system 17 which can travel over the catheter table 13 along a guide rail 21, a measuring system 25 for measuring elements which causes offsets in an X-ray irradiated field, a compensation controller 23 with a memory 31 for compensating the offsets, and a system controller 27 with a I/O terminal device 29 for controlling all systems.

Figure 2:
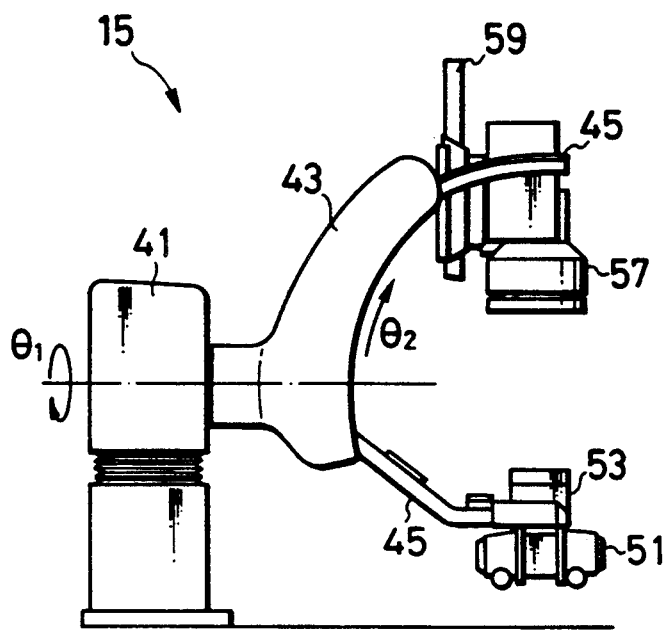
FIG. 2 is a front view of a first supporting system provided with a C-shaped holding arm.

FIG. 2 is a front view of the first supporting system 15. As shown in the figure, the first supporting system comprises a stand 41 installed on the floor, an arm holder 43 rotatably attached to the stand 41, a C-shaped holding arm 45 swingably attached to the arm holder 43. An X-ray tube 51 used as a X-ray source is attached to the end of the C-shaped holding arm 45.

An X-ray diaphragm apparatus 53 for limiting an irradiated field is mounted at the front of the X-ray tube 51.

An X-ray camera unit 55 is movably attached to the other end of the C-shaped holding arm opposing the X-ray tube, which is provided with an image intensifier 57 for intensifying an X-ray image, TV camera and a film changing unit 59 for radiographing.

Figure 3:
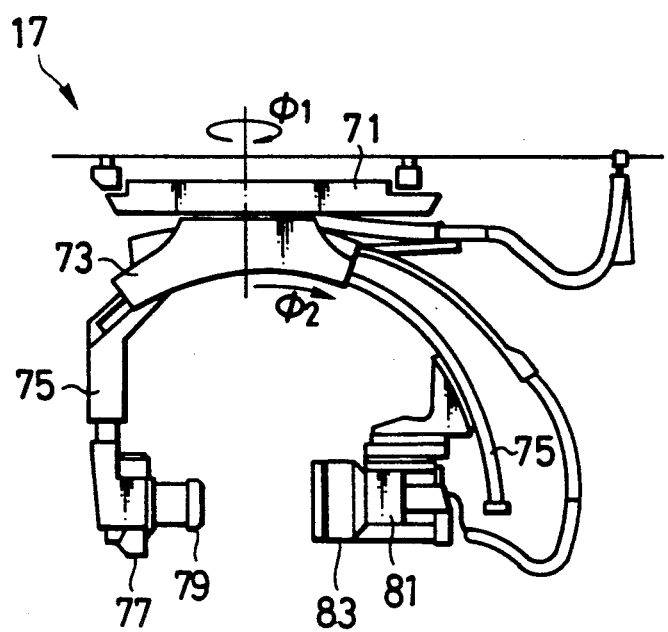
FIG. 3 is a front view of a second supporting system provided with a Ω-shaped holding arm.

FIG. 3 is a front view of the second supporting system 17. The second supporting system comprises, as shown in the figure, a vehicle 71 movably suspended from the ceiling, an arm holder 73 rotatably attached to the vehicle 71, and a Ω-shaped holding arm 75 swingably attached to the arm holder 73. An X-ray tube 77 is attached movably in the vertical direction to an end of the Ω-shaped holding arm 75. An X-ray diaphragm apparatus 79 is mounted on the front of the X-ray tube 77. A camera unit 81 is attached to the other end of the Ω-shaped holding arm 75 opposing the X-ray tube 77, freely movable in the vertical direction and in the opposing direction. The camera unit 81 is also provided with an image intensifier 83, TV camera and a film changing unit (not shown in the figure).

Figure 4A:
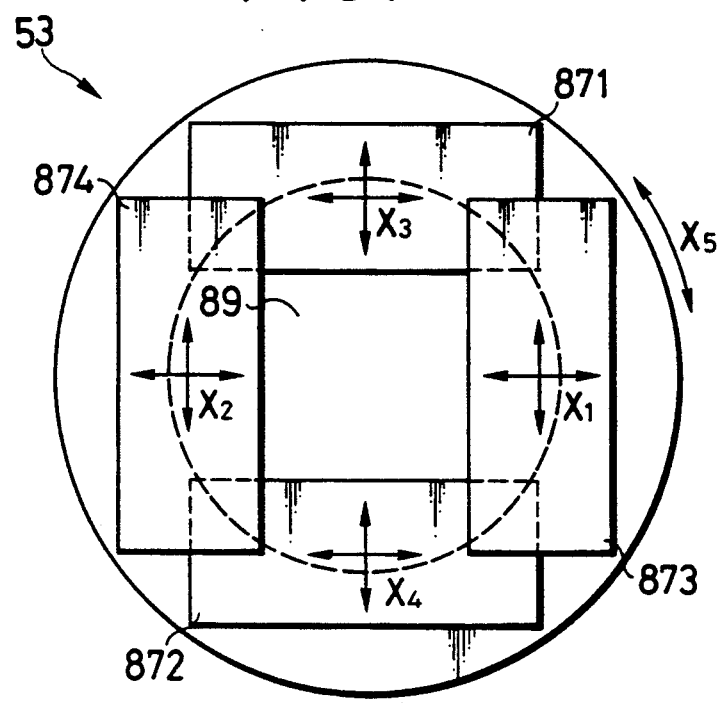
FIGS. 4A and 4B are examples of movable wings of a X-ray diaphragm apparatus.
Figure 4B:
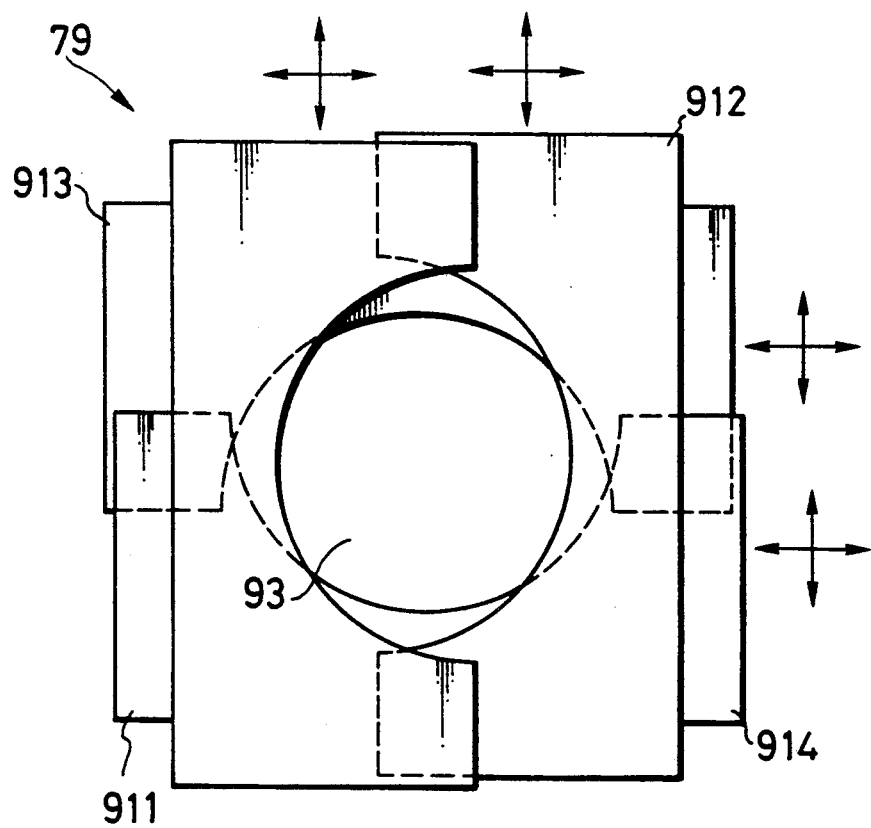

FIGS. 4A and 4B show examples of the movable wings of the X-ray diaphragm apparatus 53, 79. An X-ray diaphragm apparatus comprises four movable wings 871, 872, 873, 874 and their drive unit (not shown in the figure). Each of the movable wings shown in FIG. 4A can be moved in two directions as shown in the figure so as to form a rectangular aperture 89. These wings can also be rotated together. A wing is made of material such as lead, impervious prevents X-rays. Each of the movable wings 911, 912, 913, 914 shown in FIG. 4B can be moved in two directions as shown in the figure so as to form a substantially circular aperture 93.

A pair of wings opposing each other are moved together in an usual operation and each of the wings is moved independently for compensation. The movements of these wings are controlled by the drive unit and control signals are supplied from the system controller 27.

An advantage of the former wings is ease of manufacture. An advantage of the latter wings is that the camera units 55, 81 can be used efficiently because the front face of the camera tube of the unit is circular and unwanted X-rays are stopped. The system of the embodiment, preferably includes two types of the X-ray diaphragm above mentioned.

Figure 5:
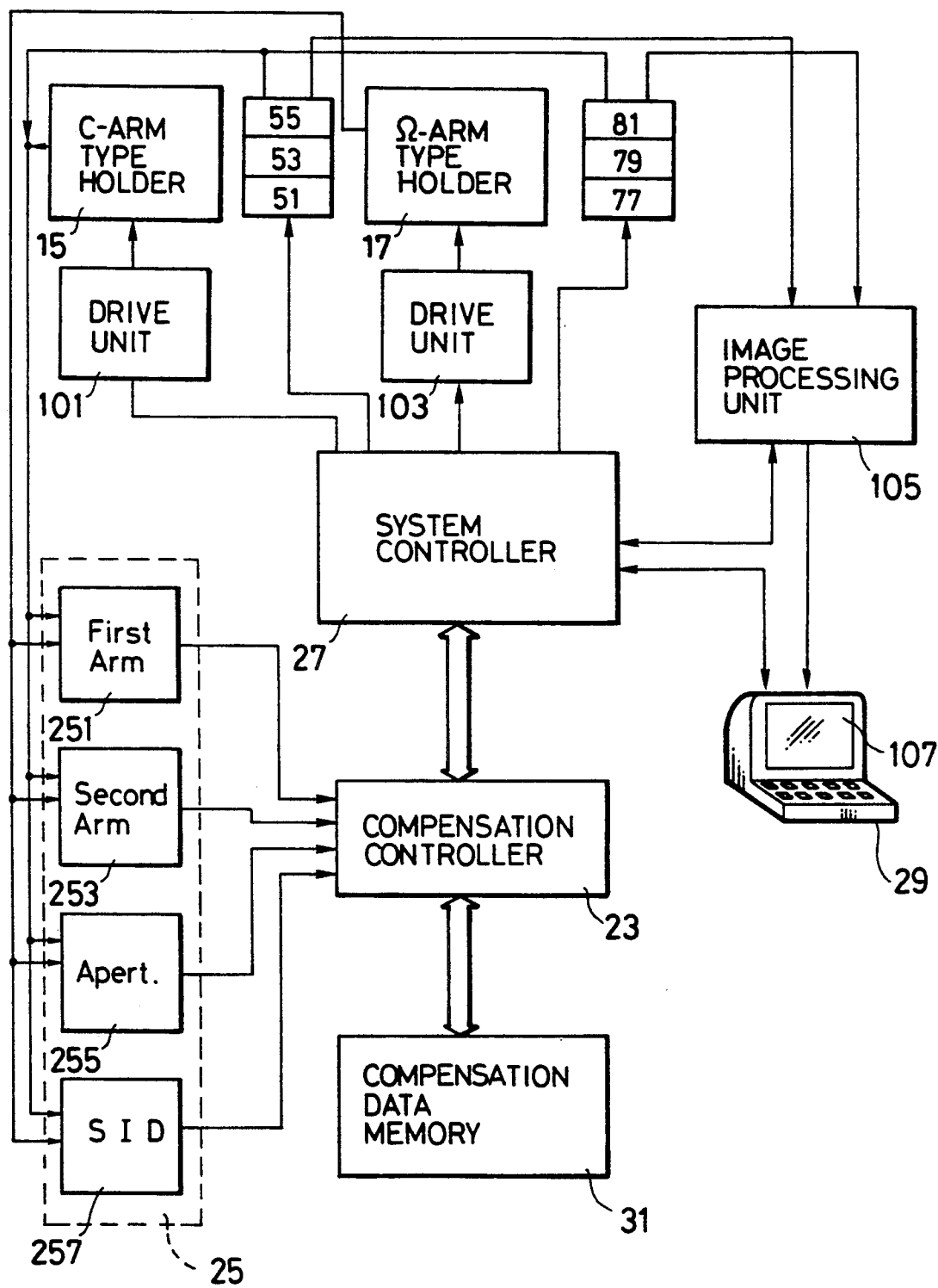
FIG. 5 shows a total control system of a first embodiment of the invention.

FIG. 5 is a total control system of the first embodiment. In the figure, the first and the second supporting systems 15, 17 are driven by drive units 101, 103. These drive units 101, 103, the X-ray tubes 51, 77 the X-ray camera units 55, 81 and the X-ray diaphragm apparatus 53, 79 are sequentially controlled by the system controller according to instruction signals input from the I/O terminal. The X-ray diaphragm is collimated according to a distance SID described below.

Image data output from the TV camera units 55, 81 are displayed on the terminal display 107. If necessary, the image data are displayed on the display after being processed by the image processing means 105.

The image processing means 105 is also controlled by the system controller 27. The measuring system 25 comprises a first angle measuring device 251, a second angle measuring device 253, an aperture measuring device 255, and a SID measuring device 257.

The first angle measuring device 251 is connected to the first and the second supporting systems 15, 17 for measuring angles of rotation angle $\theta 1$ and $\phi 1$ of the arm holders 43, 73. The second angle measuring device is connected to the supporting systems 15, 17 for measuring angles of rotation angle $\theta 2$ and $\phi 2$ of the arms 45, 75. The aperture measuring device 255 is connected to the X-ray diaphragm apparatus 53, 79 for measuring the positions of the movable wings.

The SID measuring device 257 is connected to the arms for measuring the distance between the focus of the X-ray tube and the image intensifier. This distance will be referred to SID hereinafter. The SID is a distance between the focus and a film surface when the film unit is used.

The X-ray diaphragm apparatus 53 is compensated according to the data: $\theta 1$, $\theta 2$ and its SID, and the diaphragm apparatus 79 according to the data: $\phi 1$, $\phi 2$ and its SID.

Data items measured by the measuring device 251, 253, 255, 257 are considered to be quantities which affect the offset of the X-ray irradiated field. The data output from these measuring devices is supplied to the compensation controller 23. This compensation controller 23 is connected to the compensation data memory 31 and the system controller 27. The compensation data memory 31 includes a compensating table with which the compensation amounts can be calculated based on the data measured by the measuring devices.

Figure 6A:
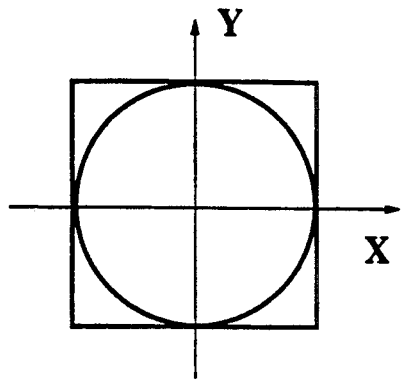
FIG. 6(A–C) show examples of offsets an X-ray irradiated field.
Figure 6B:
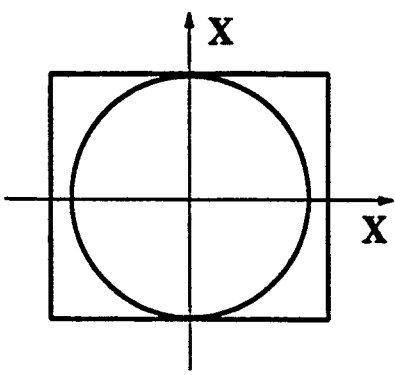
Figure 6C:
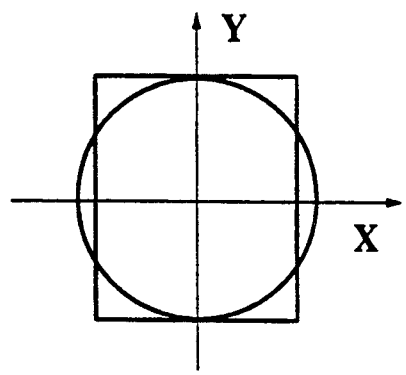
Figure 6D:
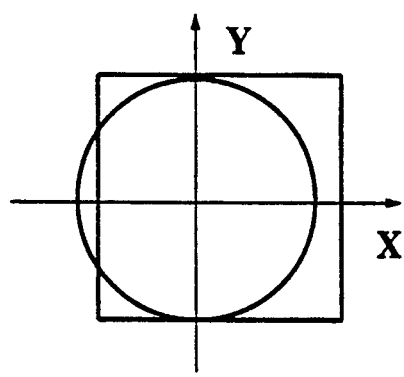
Figure 6E:
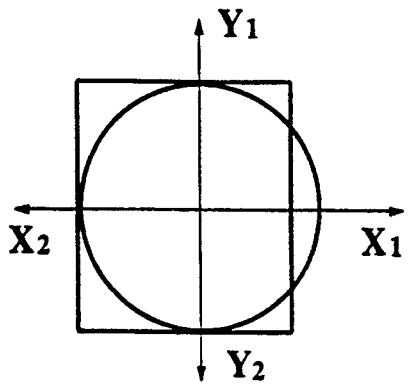
Figure 6F:
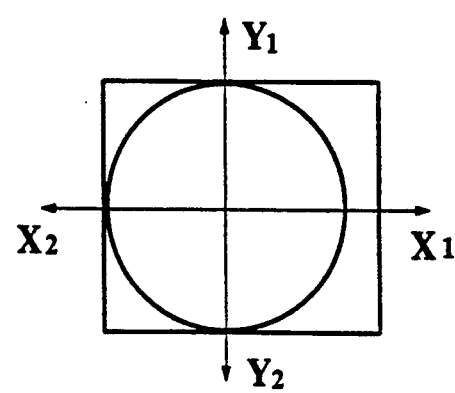

FIGS. 6A to 6F show examples of the offsets of the the X-ray irradiated field. In the figures, the solid rectangle is a X-ray irradiated field and the solid circle is the image receiving range of the X-ray camera unit. FIG. 6A shows that the field coincides with the range. FIGS. 6B to 6F show various cases of the offsets. A seeking method of compensation amounts is explained in a case where $\theta 1$, $\theta 2$ and SID are given values $\theta 1'$, $\theta 2'$ and SID'. First, the arm and the arm holder are rotated until $\theta 1$ and $\theta 2$ equal to zero. The X-ray irradiated field "F0" at this case is displayed on the display unit and the positions P0 of the X-ray diaphragm are memorized. Second, the arm and the arm holder are rotated back to the angles $\theta 1'$ and $\theta 2'$. Then, the X-ray diaphragm is adjusted watching the display until a X-ray irradiated field "F" coincides with the the field "F0". The compensation amounts at the case of $\theta 1'$, $\theta 2'$ and SID' are given by the difference of the positions between P0 and adjusted positions P.

In some case, compensation amounts are calculated upon the interpolation method with data measured already. The compensation amounts are preferably sought at both a cases where TV camera is used and where the film unit is used.

A compensation process is explained in the following. First, the case in which the compensating table has enough data for compensation will be described. In this case, the compensation amounts are calculated based on the measured data by the interpolation method or like, utilizing the table. The system controller 27 supplies the compensation instruction signal to the X-ray diaphragm apparatus 53, 79 based upon the data output from the compensating controller 23, and the movable wings of the X-ray diaphragm apparatus are adjusted to eliminate the offsets according to the instruction signal.

Second, the case which the compensating table has insufficient data to produce the compensation amount in all cases will be described. In this case, the compensation amounts are sought according the above mentioned seeking method if the compensation table can not be used. The sought compensation amounts are supplied to the system controller and stored in the compensating table. Therefore, the compensating table is gradually completed. If the table is available, the interpolation method is used.

Figure 7:
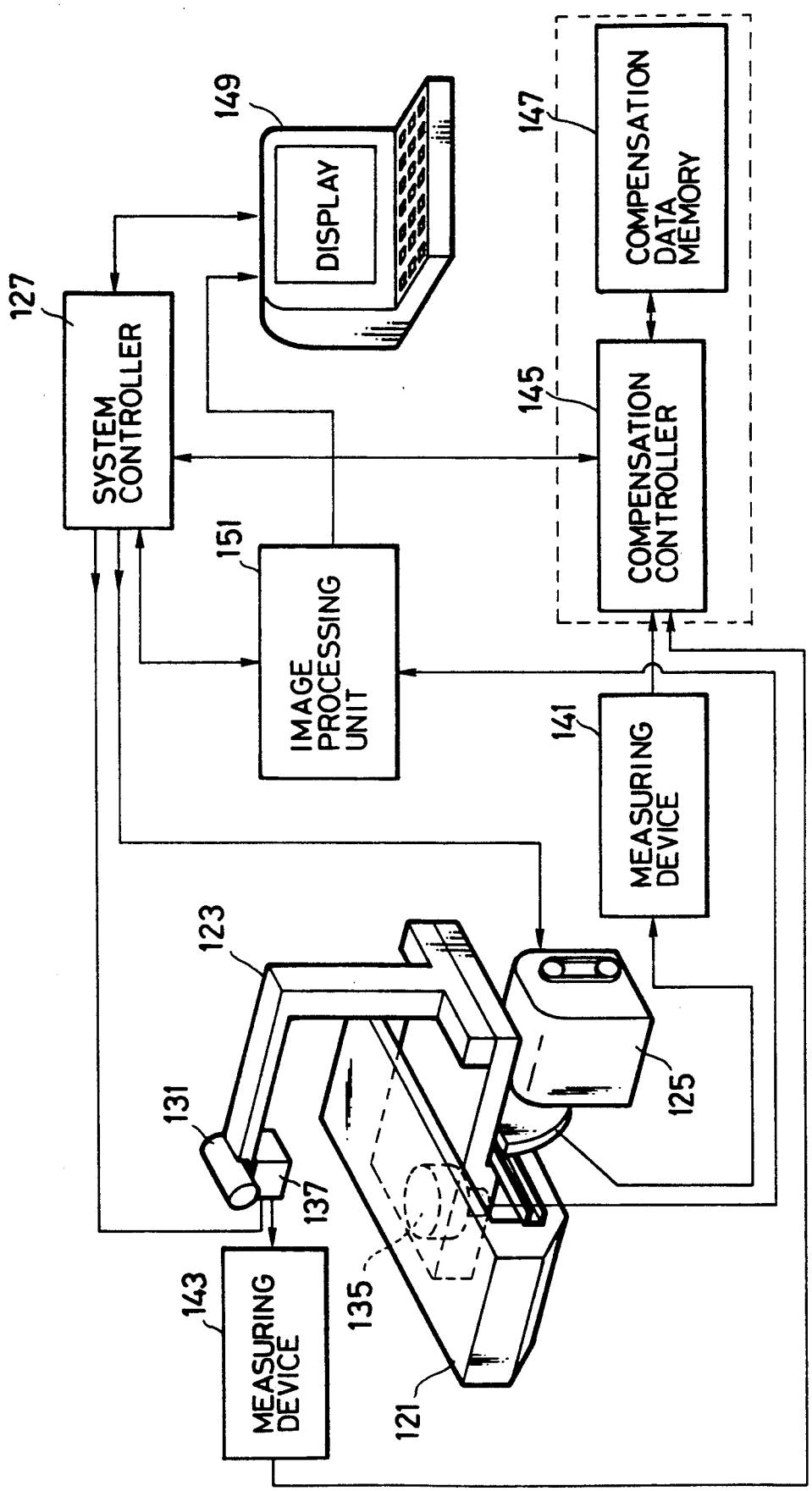
FIG. 7 shows the total system of the second embodiment of the invention.

FIG. 7 shows the total system of the second embodiment of the invention. In the figure, an X-ray diagnostic system comprises a catheter table 121 swingably mounted on the base, a supporting system 123 attached to the catheter table 121 movable in the lateral and longitudinal directions of the table, a drive unit 125 for driving the table 121 and the supporting system 123, and a system controller 127 for controlling these mechanical devices.

The supporting system 123 is formed of a flat lower part which is unbendable and a inverse L-shaped upper part which can be bent. An X-ray tube 131 is attached to the end of the L-shaped upper part. An X-ray camera unit 135 is attached to the flat lower part opposing the X-ray tube under the catheter table 121. An X-ray diaphragm apparatus 137 is mounted on the front of the X-ray tube. When the catheter table 121 is inclined, the support system is inclined together with the table so that offsets of the X-ray irradiated field are changed.

A control system for compensating the offsets comprises an angle measuring device 141 for measuring the angle of rotation of the catheter table, an aperture measuring device 143 for measuring the positions of the movable wings of the X-ray diaphragm apparatus 137, a compensation controller 145 with a compensation data memory 147 which computes compensation amounts based on the data from the angle measuring device and the aperture measuring device, utilizing a data table stored in the compensation data memory 147, and a system controller 127 with an I/O terminal device 149. In order to display radiographed pictures, the control system is provided with an image processing unit 151, which is connected to output terminal of the X-ray camera unit 135 and the display of the I/O terminal device 149 under control of the system controller 127.

The compensating process for the X-ray diagnostic system of the second embodiment constructed as mentioned above will be as follows.

First, the angle of rotation of the catheter table is measured by the angle measuring device 141 and the positions of the movable wings of the X-ray diaphragm apparatus are measured by the aperture measuring device 143. The output data are supplied to the compensation controller 145.

Second, the compensation controller 145 calculates the compensation amounts based upon the input data using the table stored in the compensation data memory 147 and sends these amounts to the system controller 127. The system controller 127 sends an instruction signal to the X-ray diaphragm apparatus 137 to adjust the positions of the movable wings according to the amount. As explained above, the present invention makes it possible to minimize the offsets of the X-ray irradiated field caused by flexing of the holding arm and to utilize a larger X-ray diagnostic system.

Various modifications will become possible for those skilled in the art after receiving the teachings of the present disclosure without departing from the scope thereof.

What is claimed is:
1. An X-ray diagnostic system comprising:
   an X-ray source including a movable X-ray diaphragm unit;
   an X-ray camera unit for radiographing a patient as an object;
   a holding means for holding the X-ray source and the X-ray camera unit in opposition and maintaining sufficient operating space between them;
   a first seeking means for seeking an offset in an X-ray irradiated field said first seeking means comprising a first measuring device for measuring an angle of rotation of the arm around an axis of the patient to be X-rayed, a second measuring device for measuring an angle of rotation of the arm in a plane including the axis, and a third measuring device for measuring a distance SID; and
   a control means for controlling the X-ray diaphragm unit according to an output of said seeking means.
2. An X-ray diagnostic system as claimed in claim 1, wherein:
   the movable X-ray diaphragm unit includes a plurality of movable wings for limiting an X-ray irradiated field.
3. An X-ray diagnostic system as claimed in claim 2, wherein:
   the controlling means is provided with a compensating table for calculating compensating amounts according to data from the seeking means.
4. An X-ray diagnostic system as claimed in claim 3, wherein:
   the control means is further provided with a second seeking means for seeking compensating amounts experimentally according to data from the first seeking means and the offsets of the X-ray irradiated field.
5. An X-ray diagnostic system as claimed in claim 1, wherein:
   the X-ray diaphragm apparatus includes four movable wings which form a rectangular aperture and can be moved to eliminate the offsets.
6. An X-ray diagnostic system as claimed in claim 1, wherein:
   the X-ray diaphragm apparatus includes four movable wings which form a substantially circular aperture and can be moved to eliminate the offsets.
7. An X-ray diagnostic system as claimed in claim 1, wherein:
   the X-ray diaphragm apparatus includes four movable wings which form a rectangular aperture and four movable wings which form a substantially circular aperture.

* * * * *